United States Patent
Joshi

(10) Patent No.: US 9,693,563 B2
(45) Date of Patent: Jul. 4, 2017

(54) BORON-SILANE POLYETHER COMPLEX

(71) Applicant: 3M INNOVATIVE PROPERTIES COMPANY, St. Paul, MN (US)

(72) Inventor: Vishalkumar Y. Joshi, Ahmedabad (IN)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/912,171

(22) PCT Filed: Aug. 11, 2014

(86) PCT No.: PCT/US2014/050485
§ 371 (c)(1),
(2) Date: Feb. 16, 2016

(87) PCT Pub. No.: WO2015/026548
PCT Pub. Date: Feb. 26, 2015

(65) Prior Publication Data
US 2016/0198718 A1    Jul. 14, 2016

(30) Foreign Application Priority Data
Aug. 20, 2013 (IN) ............................. 3676/CHE/2013

(51) Int. Cl.
| | | |
|---|---|---|
| A61K 38/47 | (2006.01) | |
| A01N 55/08 | (2006.01) | |
| A61K 33/22 | (2006.01) | |
| A01N 63/02 | (2006.01) | |
| C07F 7/18 | (2006.01) | |
| A61K 31/80 | (2006.01) | |

(52) U.S. Cl.
CPC ............. *A01N 55/08* (2013.01); *A01N 63/02* (2013.01); *A61K 31/80* (2013.01); *A61K 33/22* (2013.01); *C07F 7/1804* (2013.01)

(58) Field of Classification Search
None
See application file for complete search history.

(56) References Cited

U.S. PATENT DOCUMENTS

| | | | |
|---|---|---|---|
| 2,534,304 A | 12/1950 | Serniuk et al. | |
| 3,070,567 A | 12/1962 | Nitzsche et al. | |
| 4,255,586 A * | 3/1981 | Harrington | C07F 7/0836 252/573 |
| 5,653,972 A | 8/1997 | Desai et al. | |
| 6,849,253 B2 | 2/2005 | Chowhan et al. | |
| 2003/0127020 A1 | 7/2003 | Smith et al. | |
| 2006/0210351 A1 | 9/2006 | Losier et al. | |
| 2006/0210511 A1 | 9/2006 | Stone et al. | |
| 2010/0021562 A1 | 1/2010 | Chowhan et al. | |

FOREIGN PATENT DOCUMENTS

| | | |
|---|---|---|
| EP | 0 229 254 | 7/1987 |
| JP | 6-247815 | 9/1994 |
| WO | WO 1996/03484 | 2/1996 |
| WO | WO 01/76366 | 10/2001 |
| WO | WO 01/76647 | 10/2001 |
| WO | WO 2010/148190 | 12/2010 |
| WO | WO 2012/080628 | 6/2012 |

OTHER PUBLICATIONS

Shvarts, E.M. et al.; "Reactions of Polyols with Boric Acid and Sodium Monoborate"; Russian Journal of General Chemistry; vol. 75, No. 11; 2005; pp. 1687-1692.

* cited by examiner

*Primary Examiner* — Susan Hanley

(57) ABSTRACT

Complexes of boron and alkyl ether terminated silane polyethers are described. Compositions incorporating such complexes are also described. In addition to the boron-silane polyether complex, such compositions include water and one or more enzymes. Compositions further containing actives and/or polyols are also described. Uses for such compositions include disinfection.

20 Claims, No Drawings

BORON-SILANE POLYETHER COMPLEX

CROSS REFERENCE TO RELATED APPLICATIONS

This application is a national stage filing under 35 U.S.C. 371 of PCT/US2014/050485, filed Aug. 11, 2014, which claims priority to India Patent Application No. 3676/CHE/2013, filed Aug. 20, 2013, the disclosure of which is incorporated by reference in its entirety herein.

FIELD

The present disclosure relates to complexes of boron compounds and silane polyethers having terminal alkyl ether groups. Compositions containing such complexes, including enzymatic cleaning compositions are also described.

SUMMARY

Briefly, in one aspect, the present disclosure provides a complex of an alkyl ether-terminated silane polyether and a boron compound. In some embodiments, the alkyl ether-terminated silane polyether has the formula:

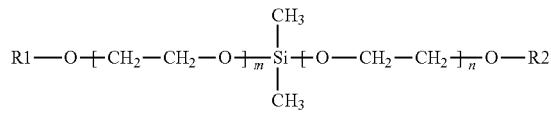

wherein m and n are independently selected integers and range from 8 to 30, and R1 and R2 are linear or branched alkyl groups having 1 to 6 carbon atoms; and wherein the boron compound is selected from the group consisting of boric acid, borax, and combinations thereof.

In some embodiments, R1 and R2 are methyl groups. In some embodiments, m and n are at least 12 and no greater than 24, e.g., in some embodiments, m and n are 18.

In some embodiments, the boron compound comprises boric acid. In some embodiments, the boron compound comprises borax.

In another aspect, the present disclosure provides a composition comprising water, at least one enzyme, and a complex of an alkyl ether-terminated silane polyether and a boron compound as described herein. In some embodiments, the molar ratio of the boron compound to the silane polyether is from 90:10 to 30:70. In some embodiments, the composition comprises at least 0.5 wt. % and no greater than 2 wt. % of the silane polyether, wherein at least a portion of the silane polyether is complexed with the boron compound. In some embodiments, the composition comprises at least 2 wt. % and no greater than 5 wt. % of the boron compound.

In some embodiments, the composition further comprising a polyol, e.g., a polyol selected from the group consisting of sugars, sugar alcohols, sugar acids, glycerol, and uronic acid, and combinations thereof. In some embodiments, the composition comprises 2 to 4 wt. % of the polyol.

In some embodiments, the enzyme is selected from the group consisting of amylases, cellulases, lipases, proteases, and combinations thereof. In some embodiments, the composition comprises a plurality of enzymes selected from at least three of amylases, cellulases, lipases, and proteases.

In some embodiments, the composition comprises an active, e.g., an active selected from the group consisting of hydrogen peroxide, aldehydes, quaternary ammonium salts, acids, and combinations thereof.

The above summary of the present disclosure is not intended to describe each embodiment of the present invention. The details of one or more embodiments of the invention are also set forth in the description below. Other features, objects, and advantages of the invention will be apparent from the description and from the claims.

DETAILED DESCRIPTION

Surface disinfection is one of the key methods used to prevent infections in hospitals. Surface disinfection is particularly important in critical areas such as the operating theater, the intensive care unit, the dialysis unit and the laboratory. Critical surfaces include floors, countertops, walls, equipment, and high touch contact areas.

Surface disinfectants may be delivered as concentrated solutions that can be diluted for use. In particular, aqueous solutions that can be diluted with 100, 200, or even 300 parts of water per part of concentrate are desired. Disinfectants may also be provided in ready-to-use form. Liquid products may be provided in spray, wipe or other forms either with or without dilution.

Surface disinfecting solutions that provide effective protection against bacteria, viruses, fungi and biological buildup together in a single formulation are particularly useful. However, many challenges exist when formulating such multi-component, multifunctional disinfectants, particularly in aqueous compositions. For example, actives, such as quaternary salts, are known to lose their activity in the presence of biological materials. It has also been accepted that quaternary ammonium biocides are instantaneously deactivated by enzymes and other proteins, as well as certain ions such those found in hard water. Thus, it is challenging to prepare a composition containing both a biocide and an enzyme.

Complexes of borax ($Na_2B_4O_7 \cdot 10H_2O$) or boric acid ($B(OH)_3$) with certain polyols have been used to stabilize compositions having both enzymes and actives together in one formulation. Such polyols have included sugars, sugar alcohols, sugar acids, glycerol, and uronic acid. In particular, complexes of borax or boric acid with glycerol have been used to stabilize enzymes and protect actives in multi-component compositions. Upon dilution, the complex releases boric acid, enzymes and actives. The boron-silane polyether complex acts as "activity protector" to protect and release enzymes to remove biological buildup. Later, chemical actives are released for their disinfection action.

Despite the availability of these polyol-based formulations, there is an on-going need for improved multifunctional disinfectants, particularly aqueous disinfectants. Particular needs include: (a) better spreading on the target surface; (b) improved film forming capability; and (c) optimized complex formation reversible on dilution.

The present inventors have discovered that certain silane polyethers may be complexed with borax or boric acid. In particular, the present inventors determined that alkyl ether terminated (e.g., methyl ether-terminated) silane polyethers can form stable, reversible complexes. Such complexes provide surprising improvements in the efficacy and stability of multi-component disinfectants, even at high dilution ratios.

In some embodiments, the silane polyethers may be represented by the following formula:

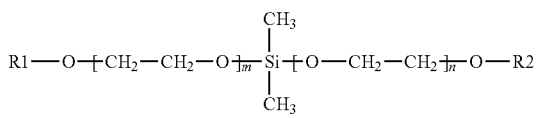

wherein m and n are independently selected integers and range from 8 to 30, and R1 and R2 are linear or branched alkyl groups. In some embodiments, m and n are at least 12, e.g., at least 16. In some embodiments, m and n are no greater than 24, e.g., no greater than 20. In some embodiments, m and n are at least 16 and no greater than 20, e.g., in some embodiments, m and n are 18, i.e., the silane polyether is a bis-(PEG-18 alkyl ether) dimethyl silane. In some embodiments, R1 and R2 have 1 to 6 carbon atoms, e.g., 1-4 carbon atoms. In some embodiments, R1 and R2 are methyl groups. In some embodiments, the silane polyether is bis-(PEG-18 methyl ether) dimethyl silane.

In some embodiments, the silane polyether may be combined with boric acid to form a complex. In some embodiments, the silane polyether may be combined with borax (also referred to as sodium borate, sodium tetraborate, and disodium tetraborate) to form a complex. In some embodiments, hydrogen-bonding and/or oxygen lone pairs may contribute to the formation on the complex.

The boron-silane polyether complexes of the present invention may be used in disinfecting compositions. The multi-component disinfecting compositions of the present disclosure include at least one enzyme. Common enzymes used in disinfectants include amylases, cellulases, lipases, proteases, and combinations thereof. In some embodiments, the disinfecting compositions include at least one enzyme selected from each of at least three of amylases, cellulases, lipases, and proteases. In some embodiments, at least one enzyme from each of these four categories is present.

In some embodiments, additional components may be included. In some embodiments, at least one active is present. Common actives used for disinfection include hydrogen peroxide, aldehydes, quaternary ammonium salts, acids, and combinations thereof.

EXAMPLES

TABLE 1

Summary of materials used in the preparation of the examples.

| Name | Description | Source and Trade name |
|---|---|---|
| Glycerol | HO-CH2-CH(OH)-CH2-OH | |
| D-glucose | (structure shown) | |
| ("SPE-1") Bis-(PEG-18 methyl ether) dimethyl silane | $H_3C-O-(CH_2-CH_2-O)_m-Si(CH_3)_2-(O-CH_2-CH_2)_n-O-CH_3$ | Dow Corning DC-2501 |
| ("SPE-2") 3-(3-Hydroxypropyl)-heptamethyl-trisiloxane, ethoxylated, acetate | (structure shown) | Dow Corning 309 |
| ("SPE-3") 3-(3-Hydroxypropyl)-heptamethyl-trisiloxane, ethoxylated, Hydroxy-terminated | (structure shown) | Dow Corning 5211 |

TABLE 1-continued

Summary of materials used in the preparation of the examples.

| Name | Description | Source and Trade name |
|---|---|---|
| ("SPE-4") 3-(3-Hydroxypropyl)-heptamethyl-trisiloxane, ethoxylated, Hydroxy-terminated | 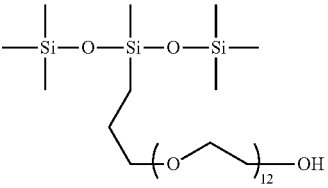 | Dow Corning 5212 |

The polyglycols and siloxane polyethers ("SPE") and were screened as complexing agents. The formulations of Table 2 were prepared by combining borax with water and heating to 50° C. Once the borax had dissolved, the solution was cooled to 40-45° C. The complexing agent was then added with stirring at room temperature for 45 minutes. The clarity of the composition was observed. The samples were stored at 55° C., and the stability as determined by solution pH was measured. Finally, after 30 days storage, the pH was measured, the samples were diluted at about 1:300 parts water and the pH was again measured. Together, a consistent pH at 1 and 30 days storage combined with a pH increase upon dilution—indicative of the formation of a reversible complex—demonstrates a stable composition.

TABLE 2

Screening various boron complexing agents.

| I.D. | Composition Parts by weight | | Clarity | pH Borax solution | pH after 1 day (55° C.) | pH after 30 days (55° C.) | pH on dilution | Comment |
|---|---|---|---|---|---|---|---|---|
| CE-1 | Borax | 3 | Yes | 9.3 | 8.2 | 8.3 | 9.1 | Stable |
|  | Glycerol | 3 | | | | | | |
|  | H2O | 60 | | | | | | |
| CE-2 | Borax | 3 | Yes | 9.3 | 7.6 | 7.6 | 8.8 | Stable |
|  | D-glucose | 3 | | | | | | |
|  | H2O | 60 | | | | | | |
| EX-1 | Borax | 3 | Yes | 9.5 | 7.9 | 7.9 | 8.9 | Stable |
|  | SPE-1 | 1 | | | | | | |
|  | H2O | 60 | | | | | | |
| CE-3 | Borax | 3 | No | 9.4 |  | N/A |  | Not stable |
|  | SPE-2 | 1 | | | | | | |
|  | H2O | 60 | | | | | | |
| CE-4 | Borax | 3 | No | 9.4 |  | N/A |  | Not stable |
|  | SPE-3 | 1 | | | | | | |
|  | H2O | 60 | | | | | | |
| CE-5 | Borax | 3 | No | 9.4 |  | N/A |  | Not stable |
|  | SPE-4 | 1 | | | | | | |
|  | H2O | 60 | | | | | | |

In some embodiments, the compositions may contain both an alkyl ether terminated silane polyether and a polyol. Suitable polyols include sugars, sugar alcohols, sugar acids, glycerol, and uronic acid. For example, in some embodiments, the composition may include glycerol. In general, the amount of polyol may depend on a variety of factors, including the particular polyol selected. In some embodiments, the composition comprises 1 to 5 wt. %, e.g., 2 to 4 wt. % of one or more polyols. Compositions containing a boron compound, an alkyl ether terminated silane polyether and a polyol were prepared and evaluated.

TABLE 3

Screening various combinations of boron complexing agents.

| I.D. | Composition Parts by weight | | Clarity | pH Borax solution | pH after 1 day | pH after 30 days | pH on dilution | Comment |
|---|---|---|---|---|---|---|---|---|
| EX-2 | Borax | 3 | Yes | 9.3 | 8.4 | 8.5 | 8.9 | Stable |
|  | Glycerol | 2.5 | | | | | | |

TABLE 3-continued

Screening various combinations of boron complexing agents.

| I.D. | Composition Parts by weight | | Clarity | pH Borax solution | pH after 1 day | pH after 30 days | pH on dilution | Comment |
|---|---|---|---|---|---|---|---|---|
| | SPE-1 | 0.5 | | | | | | |
| | H2O | 60 | | | | | | |
| EX-3 | Borax | 3 | Yes | 9.3 | 7.8 | 7.9 | 8.8 | Stable |
| | D-glucose | 2.5 | | | | | | |
| | SPE-1 | 0.5 | | | | | | |
| | H2O | 60 | | | | | | |

The presence, stability, and reversibility of the silane polyether-boron complex were evaluated using a variety of techniques.

Electrical conductivity is an effective quantitative tool to study complex formation in water for the system of a weak acid and a weak base. In the current study, the silane polyether acts as the weak acid (pH around 6) and borax acts as the weak base (pH around 9). The following analyses were carried out at 25° C. using a 20 ml solution of borax or SPE-1. Conductivity was measure at 45 minutes (immediately after complexation). The results are reported in Table 4a in units of microSiemens per centimeter (µS/cm).

TABLE 4a

Conductivity of borax and silane polyether solutions.

| | Conductivity (µS/cm) | |
|---|---|---|
| Molarity | Borax | SPE-1 |
| 0.1M | 9000 | 14 |
| 0.05M | 4530 | 11 |
| 0.01M | 1225 | 7 |
| 0.005M | 853 | 6 |
| 0.001M | 260 | 5 |
| 0.0005M | 133 | 3 |

The electrical conductivity of 0.025 M solutions of borax-SPE complex were prepared at various molar ratios of borax to silane polyether (B:S). The following analyses were carried out at 25° C. using a 20 ml solution. Conductivity was measure at 45 minutes and again after 24 hours to assess the stability of the complex. The results are summarized in Table 4b.

TABLE 4b

Conductivity of solutions containing a borax and silane polyether complex.

| Mole ratio | Conductivity (µS/cm) | | |
|---|---|---|---|
| B:S | 45 min. | 24 hours | % decrease |
| 100:0 | 9000 | 9000 | — |
| 90:10 | 9500 | 8930 | 6% |
| 70:30 | 8610 | 8600 | 0% |
| 50:50 | 6600 | 6000 | 9% |
| 30:70 | 4410 | 3970 | 10% |
| 10:90 | 2000 | 1608 | 20% |
| 0:100 | 14 | 14 | — |

As shown, the stability at mole ratios of B:S ranging from 90:10 to 30:70 was better than at a mole ratio of 10:90, with no significant difference in conductivity at a ratio of 70:30. In some embodiments, B:S mole ratios of 90:10 to 30:70 may be desired, e.g., 70:30 to 40:60.

Compositions containing various enzymes in addition to the boron-SPE complexes were prepared and evaluated for stability as summarized in Table 5. The effect of the weight percent of the alkyl ether terminated silane polyether was evaluated and compared to a comparative example using glycerol as the complexing agent. In addition to the polyether or polyol, all samples contained: (a) 3 wt. % borax; (b) 10 wt. % protease; (c) 0.2 wt. % lipase; (d) 0.11 wt. % cellulase; and (e) 1.5 wt. % alpha amylase; with the balance water.

TABLE 5

Screening various boron complexing agents in enzyme-containing compositions.

| I.D. | Complexing Agent | Wt. % | B:S* | Clarity | pH after 1 day | pH after 30 days | Comment |
|---|---|---|---|---|---|---|---|
| CE-6 | Glycerol | 3 | 80:20 | Yes | 8.2 | 7.9 | Stable |
| EX-4 | SPE-1 | 0.25 | 70:30 | No | — | — | Not stable |
| EX-5 | SPE-1 | 0.5 | 60:40 | Yes | 8.9 | 9.1 | Stable |
| EX-6 | SPE-1 | 1.0 | 40:60 | Yes | 8.9 | 8.9 | Stable |
| EX-7 | SPE-1 | 1.5 | 30:70 | Yes | 8.9 | 8.9 | Stable |

*B:S ratio for CE-6 is the molar ratio of borax to glycerol.

As shown in Table 5, for the particular formulation used, a minimum concentration silane polyether of 0.25 to 0.5 may be desirable. However, as would be recognized by one of ordinary skill in the art, the optimum amount of the polyether, as well as the desired molar ratio B:S may depend on factors such as the specific enzymes used, the particular boron compound and alkyl ether terminated silane polyether selected, and the presence of additional additives, e.g., polyols and actives. The procedures and descriptions contained herein allow such optimization to be easily performed.

In some embodiments, the disinfecting composition comprises at least 2 wt. % of the boron compound. In some embodiments, the composition comprises no greater than 5 wt. % boron compound. In some embodiments, the composition comprises 2 to 4 wt. % boron compound. In some embodiments, the disinfecting composition comprises at least 0.2 wt. % of the silane polyether. In some embodiments, the composition comprises no greater than 3 wt. % silane polyether. In some embodiments, the composition comprises 0.5 to 2 wt. % silane polyether.

UV-visible spectroscopy was use to characterized borax-SPE complex. Initially standard solutions of borax and SPE-1 were prepared and run in the spectrophotometer to establish the base line correction. These baseline samples ranged in concentration from 0.0001 M to 0.1 M borax and 0.0005 M to 0.1 M SPE-1. Next, a sample containing 0.1 M borax and 0.05 M SPE-1 (B:S=66:33) was prepared (EX-8).

This sample was diluted 100:1 with water (EX-9) and then further diluted to 10,000:1 with water (EX-10). Example EX-11 was prepared by adding enzymes to sample EX-8. This composition was then diluted 300:1 with water to form EX-12. The UV-visible spectroscopy results are summarized in Table 6.

TABLE 6

Spectroscopy results.

| Example | Results | Comments |
|---|---|---|
| CE-7 | No peaks | 0.1M borax reference solution |
| CE-8 | Two peaks at 379.9 and 383.1 nm | 0.05M SPE-1 reference solution |
| EX-8 | Single peak at 382.9 nm | 0.1M borax + 0.05 M SPE-1 Formation of complex |
| EX-9 | Two peaks at 380.8 and 383.9 nm | EX-8 diluted 100:1 with water Complex reversed on dilution with water |
| EX-10 | Two peaks at 379.9 and 383.6 nm | EX-9 diluted 100:1 with water Consistent with EX-9 |
| EX-11 | No peaks | EX-8 with enzymes Enzymes bind with the complex |
| EX-12 | No visible peaks | EX-11 diluted 300:1 with water Complex reversed and enzymes released. High absorption of the enzymes masked the SPE-1 peaks. |

The disinfecting solutions of EX-6 (borax-SPE-1 complex) and CE-6 (borax-glycerol complex) were compared. Ten microliters of water, EX-6 and CE-6 were dispensed on a glass plate and spreading was observed. Although CE-6 had a noticeably lower profile than water, a drop was still formed indicating only moderate wetting. In contrast, even after two drops of EX-6 were applied, no profile could be observed indicating exceptional spreading.

Disinfecting solutions EX-6 and CE-6 were evaluated to measure the multi-enzyme activity using standard testing protocols. The samples had comparable activity, where AU/ml=Active Units per milliliter, and KNU/ml=Kilo Novo Units per milliliter.

TABLE 7

Enzyme activity

| Sample | Protease (AU/ml) | Amylase (KNU/ml) |
|---|---|---|
| EX-6 | 0.307 | 5.655 |
| CE-6 | 0.314 | 5.603 |

The enzyme-containing disinfecting solutions of EX-6 and CE-6 were evaluated using a BROWNE STF Load Check Strip. The load check strip is printed with a bright red soil formula said to contain two sources of protein, lipids and polysaccharides, and is said to have equivalent performance to the Edinburgh Test Soil described in EN ISO 15882-5. The solutions were first diluted 300:1 with water and the cleaning test was conducted for five minutes at 45° C. Based on this test, even though they had comparable enzyme activities, the disinfecting solution of EX-6 produced superior results with only a small light red region remaining, compared to the larger dark red area remaining when the CE-6 solution was used.

Various modifications and alterations of this invention will become apparent to those skilled in the art without departing from the scope and spirit of this invention.

The invention claimed is:

1. A complex of an alkyl ether-terminated silane polyether and a boron compound, wherein the alkyl ether-terminated silane polyether has the formula:

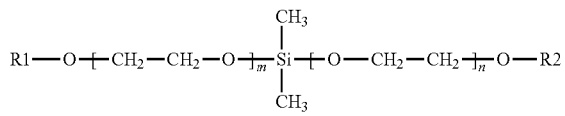

wherein m and n are independently selected integers and range from 8 to 30, and R1 and R2 are linear or branched alkyl groups having 1 to 6 carbon atoms; and wherein the boron compound is selected from the group consisting of boric acid and borax.

2. The complex of claim 1, wherein R1 and R2 are methyl groups.

3. The complex of claim 1, wherein m and n are each at least 12 and no greater than 24.

4. The complex of claim 3, wherein m and n are each at least 16 and no greater than 20.

5. The complex of claim 4, wherein m and n are each 18.

6. The complex of claim 1, wherein the boron compound is boric acid.

7. The complex of claim 1, wherein the boron compound is borax.

8. A composition comprising water, at least one enzyme, and the complex according to claim 1.

9. The composition of claim 8, wherein the molar ratio of the boron compound to the silane polyether is from 90:10 to 30:70.

10. The composition of claim 9, wherein the molar ratio of the boron compound to the silane polyether is from 70:30 to 40:60.

11. The composition of claim 8 comprising at least 0.5 wt. % and no greater than 2 wt. % of the silane polyether, wherein at least a portion of the silane polyether is complexed with the boron compound.

12. The composition of claim 8 comprising at least 2 wt. % and no greater than 5 wt. % of the boron compound.

13. The composition of claim 8, further comprising a polyol.

14. The composition of claim 13, wherein the polyol is selected from the group consisting of sugars, sugar alcohols, sugar acids, glycerol, and uronic acid, and combinations thereof.

15. The composition of claim 14, wherein the polyol is selected from the group consisting of glycerol, glucose, and combinations thereof.

16. The composition of claim 13 comprising 2 to 4 wt. % of the polyol.

17. The composition of claim 8, wherein the enzyme is selected from the group consisting of amylases, cellulases, lipases, proteases, and combinations thereof.

18. The composition of claim 17 comprising a plurality of enzymes selected from at least three of amylases, cellulases, lipases, and proteases.

19. The composition of claim 8, further comprising an active selected from the group consisting of hydrogen peroxide, aldehydes, quaternary ammonium salts, acids, and combinations thereof.

20. The composition of claim 8, wherein the pH of the composition increases by at least 1 upon dilution with 300 parts water per 1 part of the composition.

* * * * *